United States Patent
Beran et al.

(12) 
(10) Patent No.: US 11,911,576 B2
(45) Date of Patent: Feb. 27, 2024

(54) FLEXIBLE UNIVERSAL CATHETER SECUREMENT DEVICE

(71) Applicant: B. Braun Medical, Inc., Bethlehem, PA (US)

(72) Inventors: Anthony V Beran, Yorba Linda, CA (US); Kerry J Tomic-Edgar, Yorba Linda, CA (US)

(73) Assignee: B. Braun Medical, Inc., Bethlehem, PA (US)

( * ) Notice: Subject to any disclaimer, the term of this patent is extended or adjusted under 35 U.S.C. 154(b) by 71 days.

(21) Appl. No.: 16/570,862

(22) Filed: Sep. 13, 2019

(65) Prior Publication Data
US 2021/0077782 A1 Mar. 18, 2021

(51) Int. Cl.
*A61M 25/02* (2006.01)

(52) U.S. Cl.
CPC ....... *A61M 25/02* (2013.01); *A61M 2025/026* (2013.01); *A61M 2025/0246* (2013.01); *A61M 2025/0273* (2013.01)

(58) Field of Classification Search
CPC .... A61M 2025/0246; A61M 2025/026; A61M 2025/0266; A61M 25/02; A61M 2025/0253
See application file for complete search history.

(56) References Cited

U.S. PATENT DOCUMENTS

| | | | | |
|---|---|---|---|---|
| 4,490,141 A | * | 12/1984 | Lacko | A61M 25/02 128/DIG. 26 |
| 4,702,736 A | * | 10/1987 | Kalt | A61M 25/02 128/DIG. 26 |
| 5,304,146 A | * | 4/1994 | Johnson | A61M 25/02 128/DIG. 26 |
| D845,471 S | | 4/2019 | Kyvik | |
| D846,114 S | | 4/2019 | Kyvik | |
| 2018/0050175 A1 | * | 2/2018 | Souza | A61F 13/0246 |
| 2018/0154118 A1 | | 6/2018 | Kyvik | |

* cited by examiner

*Primary Examiner* — Deanna K Hall
(74) *Attorney, Agent, or Firm* — Christopher A Rothe; Culhane Meadows PLLC

(57) ABSTRACT

The present invention pertains to a flexible universal catheter securement device for use with, e.g. Foley catheters and other catheters. The flexible universal catheter securement device preferably comprises a cover attached to a base at a longitudinal articulation point. The cover has a top cover surface and a bottom cover surface and the bottom cover surface has an adhesive foam padding. The base has a top base surface and a bottom base surface and the top base surface has an adhesive foam padding. The articulation point is foldable such that the cover can be placed on the base. The base and the cover preferably have a centerline and the articulation point is offset there from. The base further comprises a catheter placement axis and the longitudinal articulation point is located parallel to the catheter placement axis. The cover preferably has less surface area than the base.

6 Claims, 18 Drawing Sheets

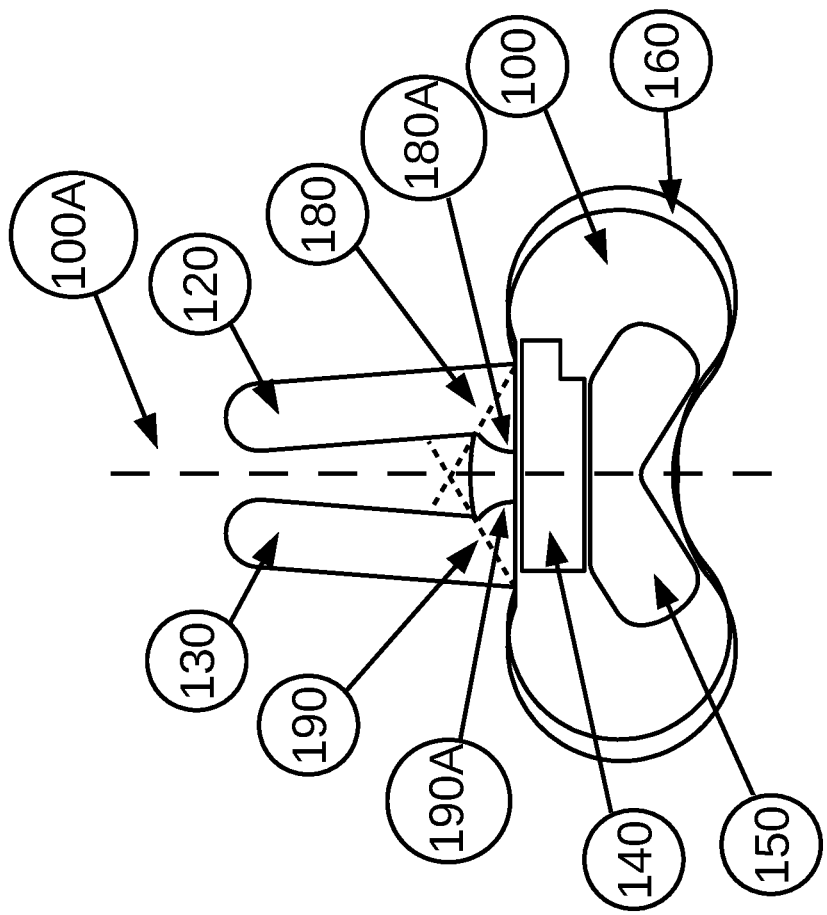

FLEXIBLE UNIVERSAL CATHETER SECUREMENT DEVICE

TECHNICAL FIELD

The present invention pertains to a flexible universal catheter securement device for use with, e.g. Foley catheters and other catheters.

BACKGROUND ART

Medical devices, such as a catheter's tubes and lines, often must be used in patients and left in place for many days. These devices must be properly secured to prevent catheter dislodgement, to prevent catheter movement within the insertion site, to be atraumatic and comfortable to the patient and to provide user-friendly and easy application and removal. Presently, in clinical applications at a catheter insertion site, an external portion of a catheter and a securement device are covered with a bio-occlusive dressing, such as Tegaderm®, to protect the catheter insertion site. It is important that, in such an application, the securement device is soft and pliable with a low profile and, at the same time, meets the above-mentioned catheter securement requirements. Thus, a device that provides these requirements is desired.

SUMMARY OF THE INVENTION

The present invention pertains to a flexible universal catheter securement device for use with, e.g. Foley catheters and other catheters. The flexible universal catheter securement device preferably comprises a cover attached to a base at a longitudinal articulation point. The cover has a top cover surface and a bottom cover surface and the bottom cover surface has an adhesive foam padding. The base has a top base surface and a bottom base surface and the bottom base surface has an adhesive foam padding. The articulation point is foldable such that the cover can be placed on the base. The base and the cover preferably have a centerline and the articulation point is offset there from. The base further comprises a catheter placement axis and the longitudinal articulation point is located parallel to the catheter placement axis and is in direction of a pull force exhibited during catheter application, therefor mechanically preventing catheter dislodgement. The cover preferably has less surface area than the base. Hook and loop material, e.g. Velcro®, can be substituted for adhesive padding.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 15A is a top view of an alternative embodiment of the invention in an open position;

DETAILED DESCRIPTION OF THE PREFERRED EMBODIMENTS

Figure 1B:
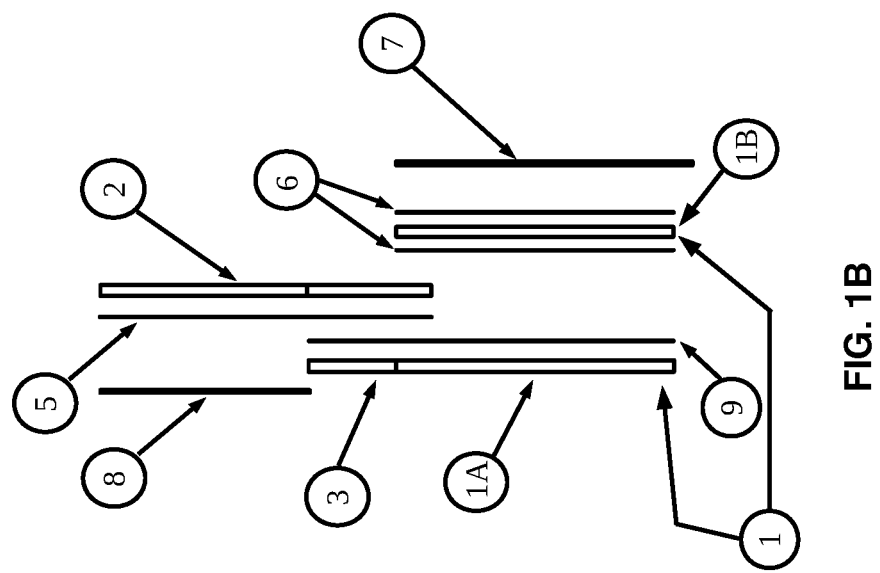
FIG. 1B is a side exploded view of a preferred embodiment of the invention.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved flexible universal catheter securement device.

Figure 1A:
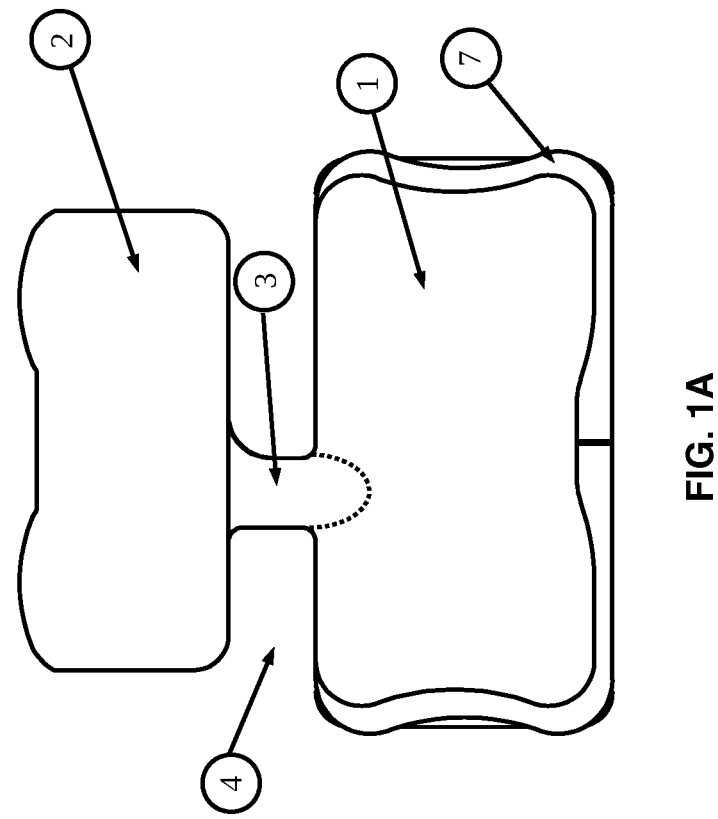
FIG. 1A is a top view of a preferred embodiment of the invention in the open position.

Referring now to FIGS. 1A and 1B, a preferred embodiment of a securement device for securing a Foley catheter or other catheter device is shown. The invention has a base 1 separated from the cover 2, by a partial gap 4 and connected to the cover 2 by an articulation point 3. Preferably, base 1 and cover 2 comprise adhesive foam padding. The base 1 comprises a first base 1A and second base 1B. First base 1A preferably has an adhesive foam pad 9 on its bottom surface and second base 1B preferably has adhesive pads 6 on the top and bottom surface. The articulation point 3 is preferably sandwiched between first base 1A and second base 1B, securing articulation point 3 on both sides with adhesive 9 from the bottom surface of first base 1A and adhesive 6 from the top surface of second base 1B. The bottom surface of second base 1B also preferably has an adhesive 6, so that base 1 can be attached/adhered to a patient. The cover 2 also preferably has an adhesive layer 5 (shown in FIG. 1B). The adhesive layer 6 is placed on the bottom surface of the base 1 and the adhesive layer 5 placed on the top surface of the cover 2. The adhesive layer 6 at the bottom surface of the base 1 is preferably covered with a double folded release liner 7 to facilitate an easy placement of a device on the patient. The adhesive layer 5 is also covered with a release liner 8 that is removed during application of the device to a patient and securement of a catheter.

Figure 16B:
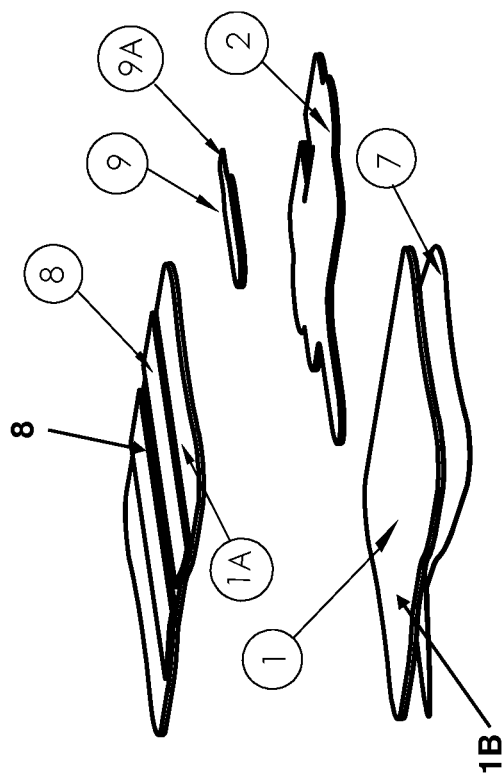
FIG. 16A is a top view of an alternative embodiment of the invention in an open position; and, FIG. 16B is side exploded perspective view of the embodiment in FIG. 16A.
Figure 16A:
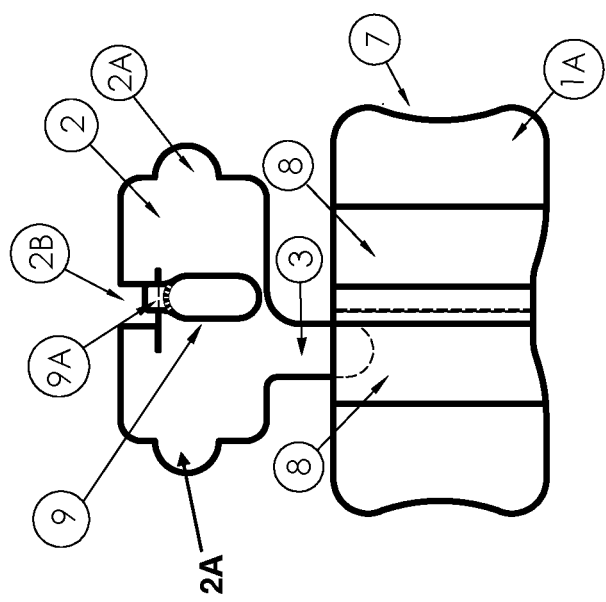

Referring now to FIGS. 16A and 16B, another embodiment of a securement device is shown. In this alternative embodiment, the cover 2 is made has a removable Velcro® loop material. This embodiment preferably has a base 1 and a cover 2, which are separated by a gap and connected by an articulation point 3. The base 1 preferably comprises first base layer 1A and a second base layer 1B. The second base layer 1B preferably has a top surface and a bottom surface, where both surfaces, preferably have an adhesive layer. The first base layer 1A preferably has a top and bottom surface, but only the bottom surface is covered with adhesive. The cover 2 preferably comprises a Velcro® loop material on the bottom surface of the cover 2. The articulation point 3 is preferably sandwiched between second base layer 1B and first base layer 1A, securing the articulation point 3 on both sides with adhesive from a top surface of second base layer 1B and a bottom surface of first base layer 1A. There are preferably two hook material (e.g. Velcro®) strips 8 placed on the top of first base layer 1A for removable attachment of cover 2 to first base layer 1A. The cover 2 preferably has a slot 2B, which provides for a better fit around an outside circumference of a catheter (not shown in FIGS. 16A and 16B). The cover 2 also preferably has a foam pad 9 with an adhesive on its top and bottom surface. The bottom surface adhesive on foam pad 9 preferably secures the pad 9 to the bottom surface of cover 2. The top surface of foam pad 9 is preferably covered with a release liner 9A. The release liner 9A is preferably removed during application of the device and secures the device to the top surface of a catheter. The cover 2 also preferably has two tabs 2A for easier separation of cover 2 from first base layer 1A. Second base layer 1B preferably has a release liner 7 covering adhesive on second base layer 1B. The release liner 7 is preferably removed to secure the base 1 to a patient's skin during application of the device.

Figure 2:
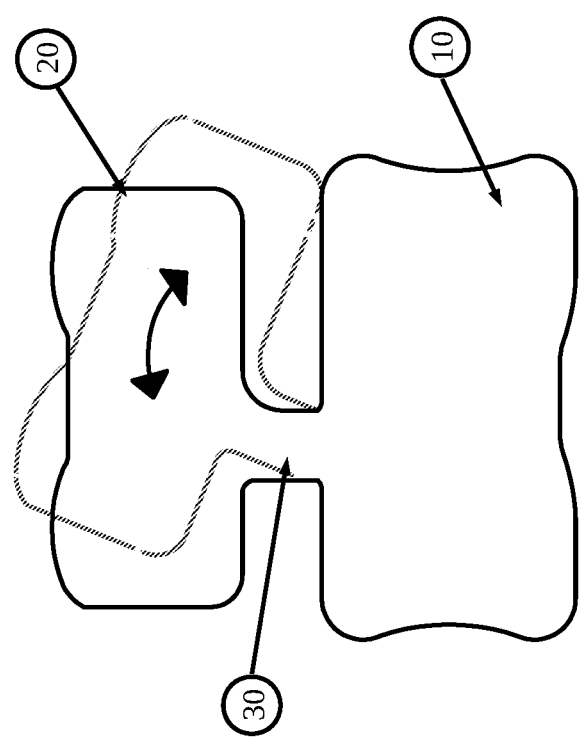
FIG. 2 is a top view of a preferred embodiment of the invention showing articulation of the cover.

Referring now to FIG. 2, the cover 20 for the embodiment shown in FIGS. 1A and 1B is shown with lateral articulation (shown by arrows) related to the fixed base 10 at the articulation point 30.

Figure 3:
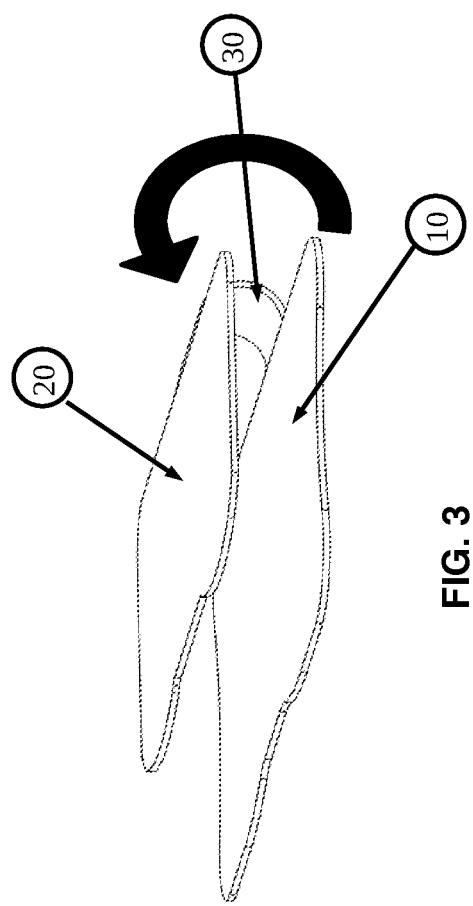
FIG. 3 is a side perspective view of a preferred embodiment of the invention.

Referring now to FIG. 3, the cover 20 for the embodiment shown in FIGS. 1A and 1B is shown with longitudinal articulation at the articulation point 30, moving in the preferred direction (shown by arrows) to close the cover 20 over the base 10. This closing of the cover 20 can secure a catheter (not shown in FIG. 3) between the cover 20 and the base 10. The articulation point 30 is preferably in the direction of, or parallel with, the catheter placement. It is at 0 degrees to the catheter axis. It is not at 90 degrees to the catheter axis like other securement devices.

Figure 4B:
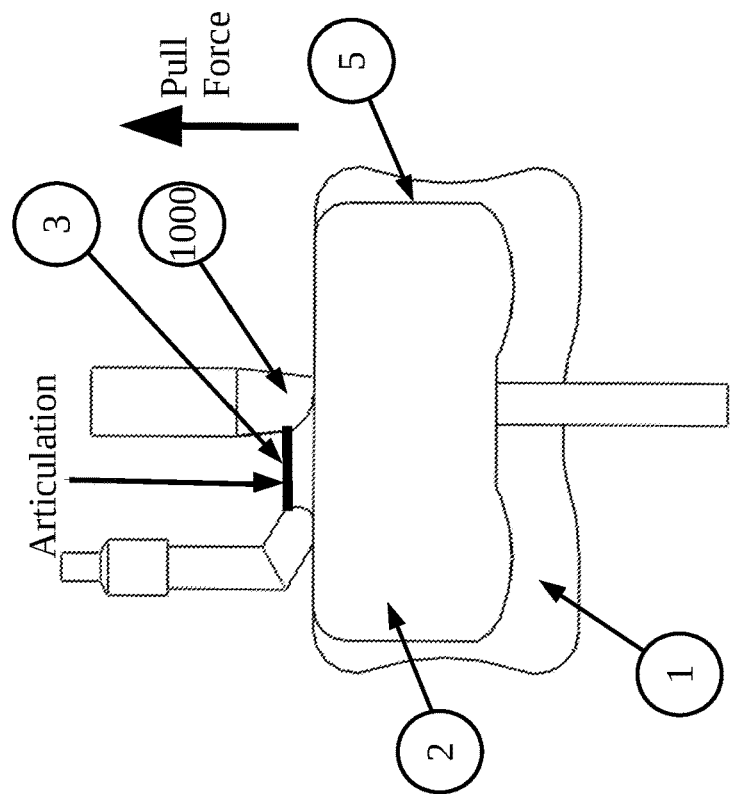
FIG. 4B is a top view of a preferred embodiment of the invention in a closed position securing a catheter.
Figure 4A:
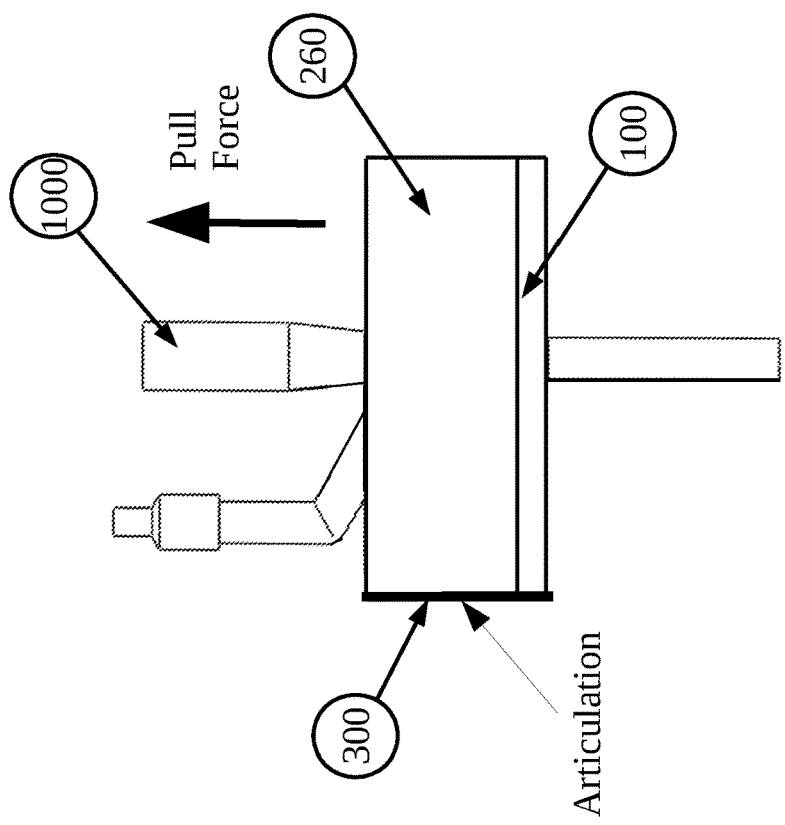
FIG. 4A is a prior art catheter securement device.

Referring now to FIG. 4A, the figure shows a prior art catheter securement device. The catheter 1000 is secured between the base 100 and the cover 200 by adhesion force produced by an adhesive, which is in contact with the catheter 1000. The device opens and closes by lateral movement at the articulation point 300, which is perpendicular to the catheter axis as shown in FIG. 4A. Thus, only adhesive force is used to secure the catheter 1000 between the base 100 and the cover 200 in the prior art example.

Referring now to FIG. 4B, a preferred embodiment of the invention is shown with a catheter 1000 secured. As is shown in FIG. 4B, the catheter 1000 is secured between the base 1 and the cover 2 by adhesion force produced by an adhesive 5, which is in contact with the catheter 1000 and by a mechanical resistor/barrier produced by the articulation point/structure 3, which prevents movement of the catheter 1000 in the direction of pull force (direction of arrow). The device preferably opens and closes by longitudinal movement of the articulation point 3, which is at the catheter's bifurcation and is aligned on the axis of the catheter. Thus, the present invention provides for lateral and longitudinal securement of the catheter 1000 by mechanical and adhesion forces.

Figure 5:
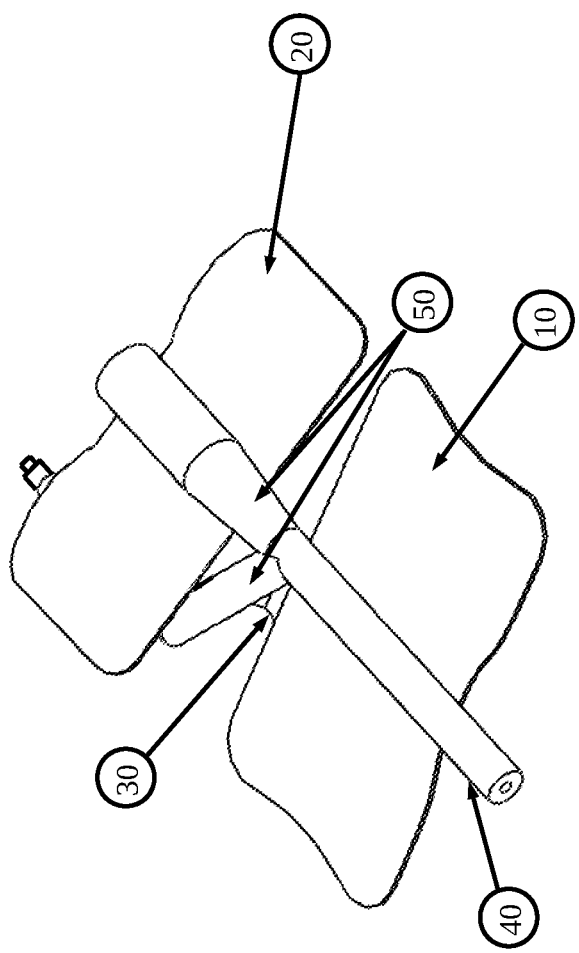
FIG. 5 is a top perspective view of a preferred embodiment of the invention with the cover partially articulated between the catheter's bifurcation.
Figure 6:
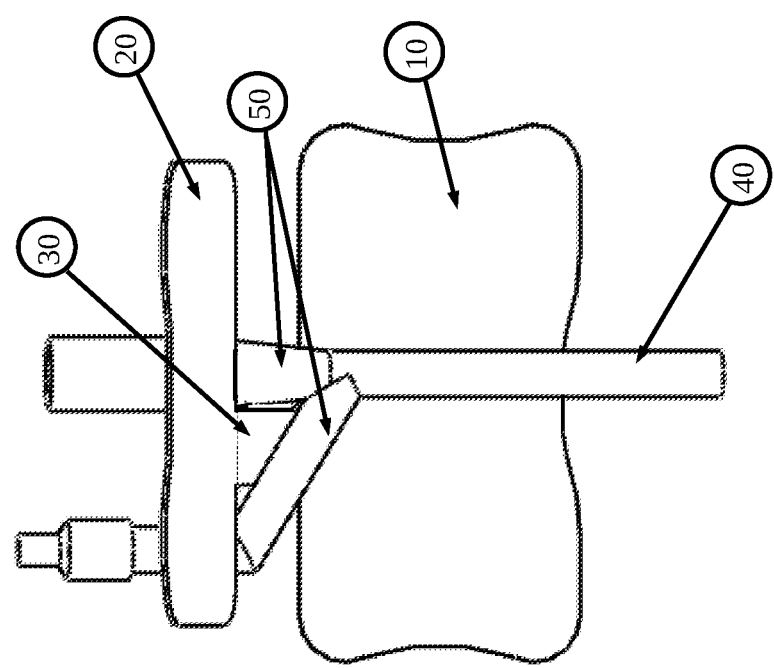
FIG. 6 is a top view of a preferred embodiment of the invention in an open position with an articulation point between the catheter's bifurcation.
Figure 7:
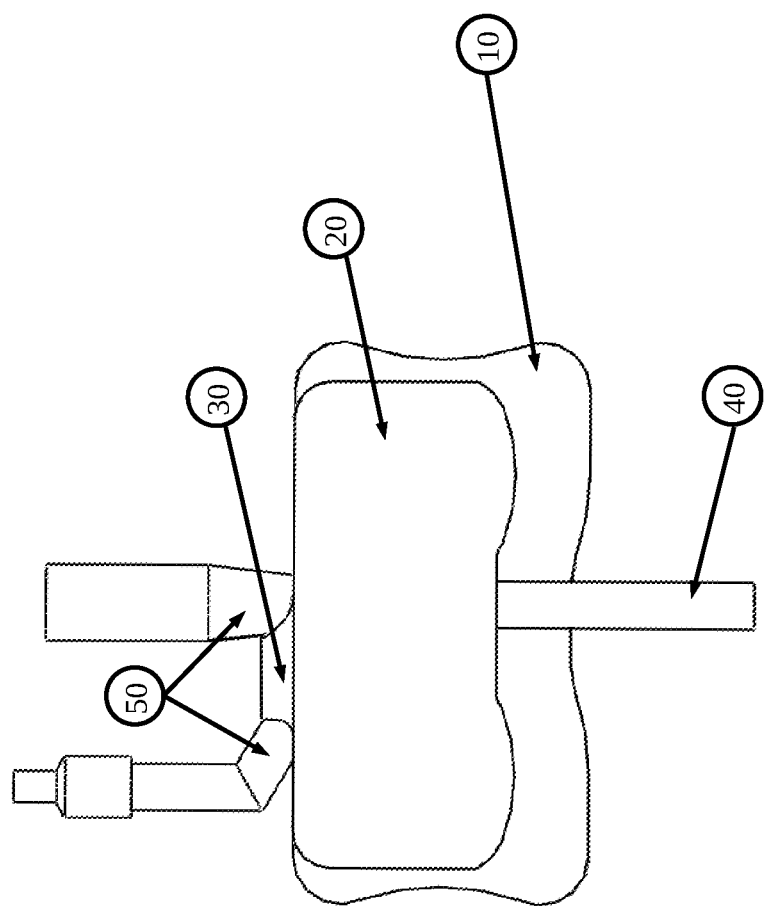
FIG. 7 is a top view of a preferred embodiment of the invention in a closed position securing a catheter.

Referring now to FIG. 5, a catheter 40 is placed on the base 10 and over the cover 20. By longitudinal and lateral movement at the articulation point 30, the cover 20, through the catheter's bifurcation 50, is placed over the catheter 40 (shown also in FIG. 6) and secured to the top side of the base 10, locking the catheter 40 in place between the cover 20, base 10 and the articulation point 30 (as also shown in FIG. 7). The articulation point 30, when placed over the catheter's bifurcation 50, prevents or resists dislodgement of the catheter 40 related to the longitudinal pull force (direction of arrow shown in FIG. 4B), while the adhesion of the cover 20 to the base 10 prevents or resists catheter dislodgement related to a lateral pull force (not shown).

Figure 8B:
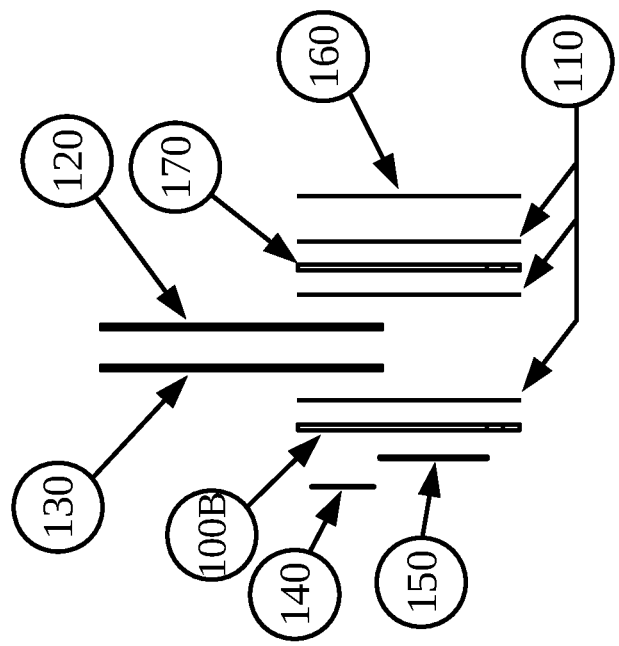
FIG. 8B is a side exploded view of an alternative embodiment of the invention.
Figure 8A:
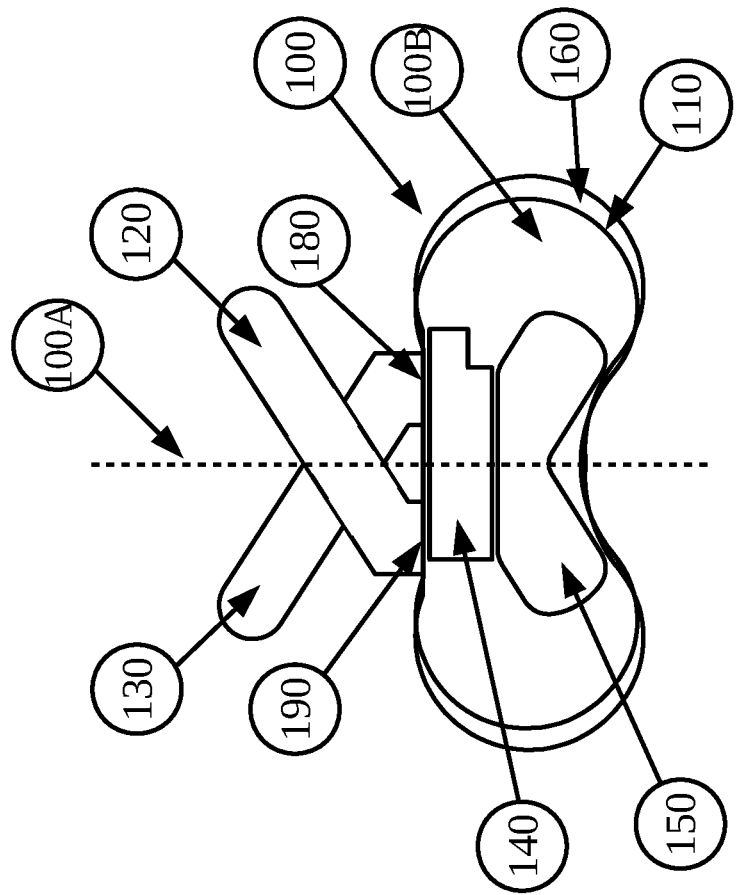
FIG. 8A is a top view of an alternative embodiment of the invention in an open position.

Referring now to FIG. 8A and FIG. 8B, an alternative embodiment of a flexible catheter securement device for multiple types of catheters is shown. The device preferably comprises a base 100 to which two crossed straps 120 and 130 preferably comprising Velcro® loop material are attached and form fixed angle articulation points 180 and 190 between the straps 120, 130 and the base 100. The straps 120 and 130, when in an opened position, cross a virtual center line 100A of the device and form a chevron position when engaged with a hook material 150 of base 100. A base 100, preferably has two pads, a top pad 100B with an adhesive 110 on its bottom surface and a bottom pad 170, with an adhesive 110 on the top and bottom surfaces. The straps 120 and 130 are secured between the top pad 100B and 170. The bottom surface of bottom pad 170 is preferably at least partially covered with a hypoallergenic adhesive layer 110, preferably for attaching the device to a patient's skin. The top side of the base, top pad 100B, preferably has a sticky portion 140. The sticky portion 140 can be in the form of double sided adhesive tape or any other sticky surface such as an adhesive. The sticky portion 140 is preferably used to stabilize a catheter (not shown in 8A or 8B) on the base 100 during the securement process. In addition, a hook portion 150, e.g. Velcro®, is shown attached to the top surface of the base 100. The cross straps 120 and 130 preferably comprise a loop portion, e.g. Velcro®, for simplified mating with the hook portion 150 of the base 100. The bottom adhesive surface 110 of the bottom pad 170 is preferably covered with a paper release liner 160 for simplified application of the device to a patient's skin.

Figure 9:
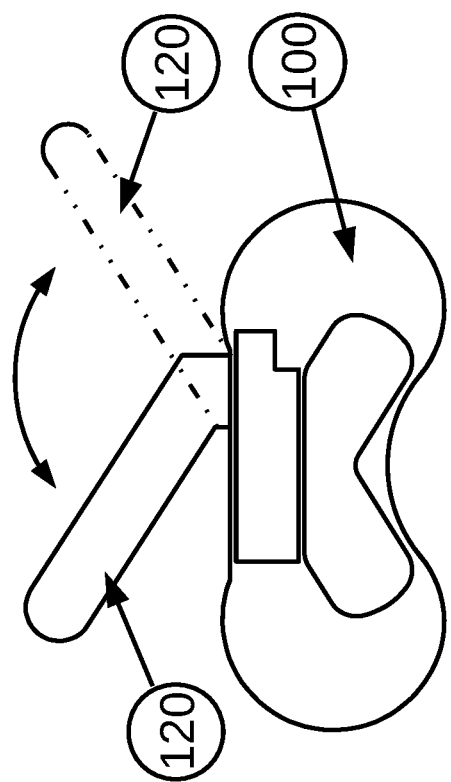
FIG. 9 is a top partial view of an alternative embodiment of the invention showing lateral articulation.
Figure 10:
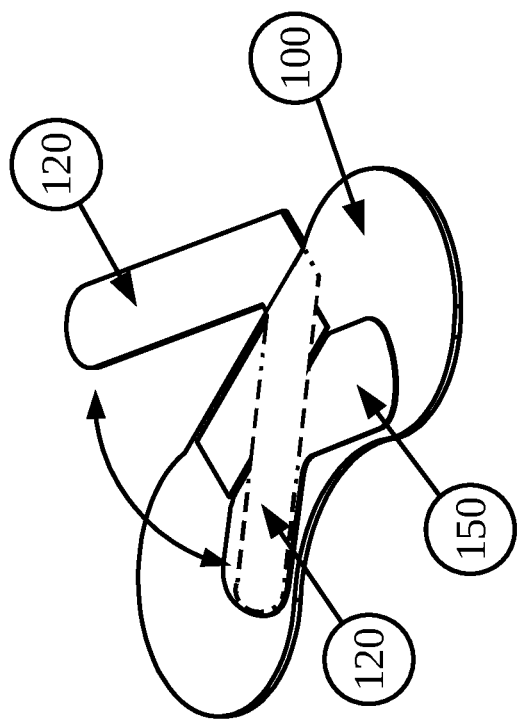
FIG. 10 is a top perspective view of an alternative embodiment of the invention showing longitudinal articulation.

Referring now to FIG. 9, the strap 120 for the embodiment shown in FIG. 8A is shown with lateral articulation in relationship to the base 100. Referring now to FIG. 10, the strap 120 for the embodiment shown in FIG. 8A is shown with a longitudinal articulation, moving in an opposite direction to mate with the hook portion 150 of the base 100.

Figure 11:
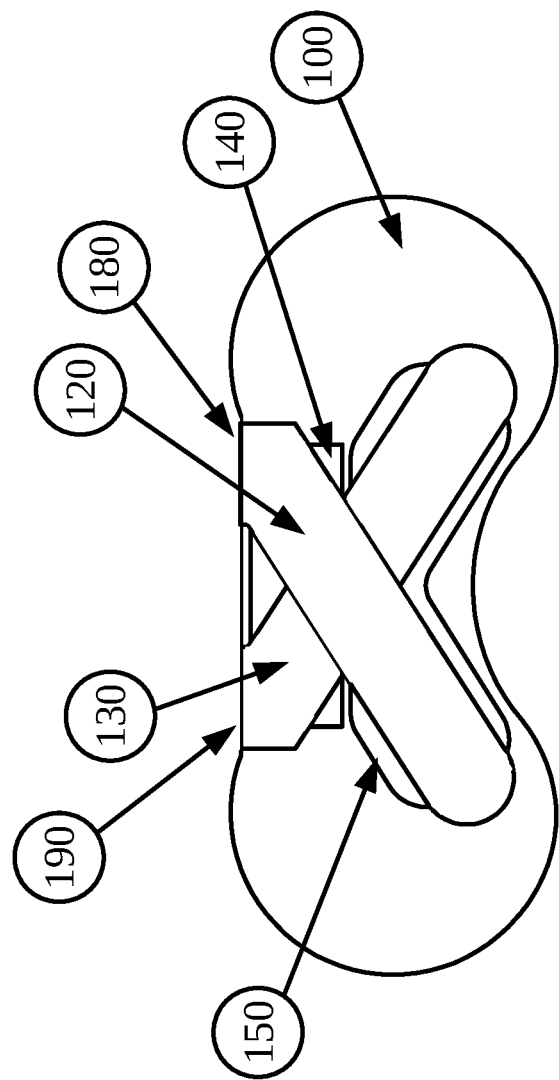
FIG. 11 is a top view of an alternative embodiment of the invention in a closed position.

Referring now to FIG. 11, a top view of the alternative embodiment from FIGS. 8A-10 is shown in a closed position. The straps 120 and 130 are shown in a closed or cross/chevron position, mating with the hook portion 150 of the base 100. The articulation points 180 and 190 of straps 120 and 130 at the interconnection with the base 100 are shown in a longitudinal direction of catheter placement (catheter not shown). The articulation points 180 and 190 are shown at a zero degree angle to the catheter axis.

Figure 12:
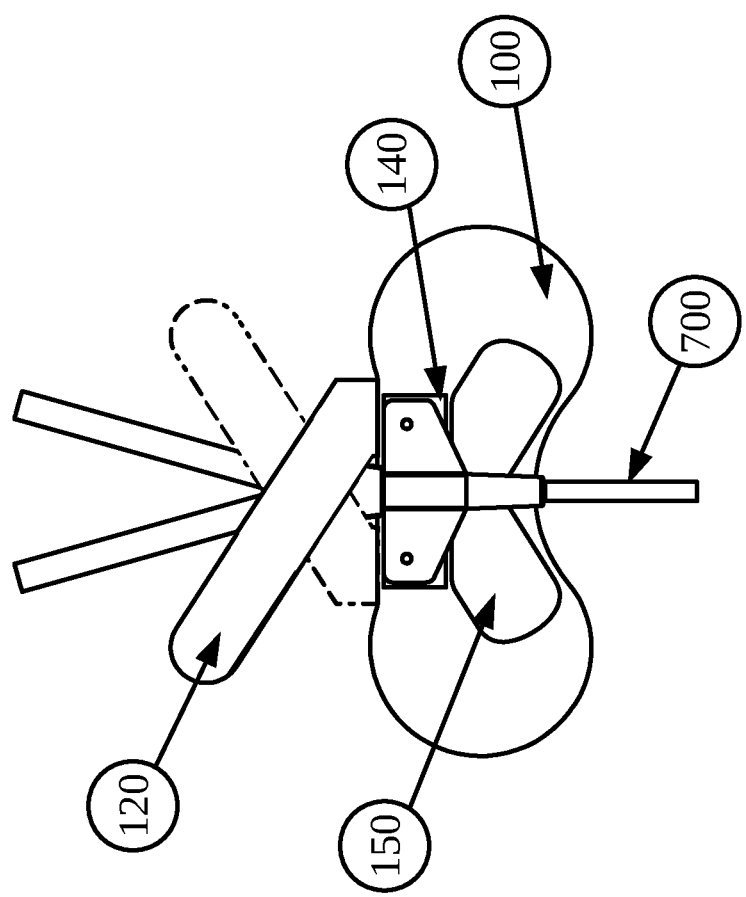
FIG. 12 is a top view of an alternative embodiment of the invention showing articulation of the straps with a winged catheter in the device.

Referring now to FIG. 12, a view of the alternative embodiment is shown in a clinical application. A wing portion of a catheter 700 is placed over the base 100 and sticky portion 140. By longitudinal and lateral articulation of strap 120 in relationship to the base 100, the strap 120 is brought from below the catheter 700 to above the catheter 700.

Figure 13:
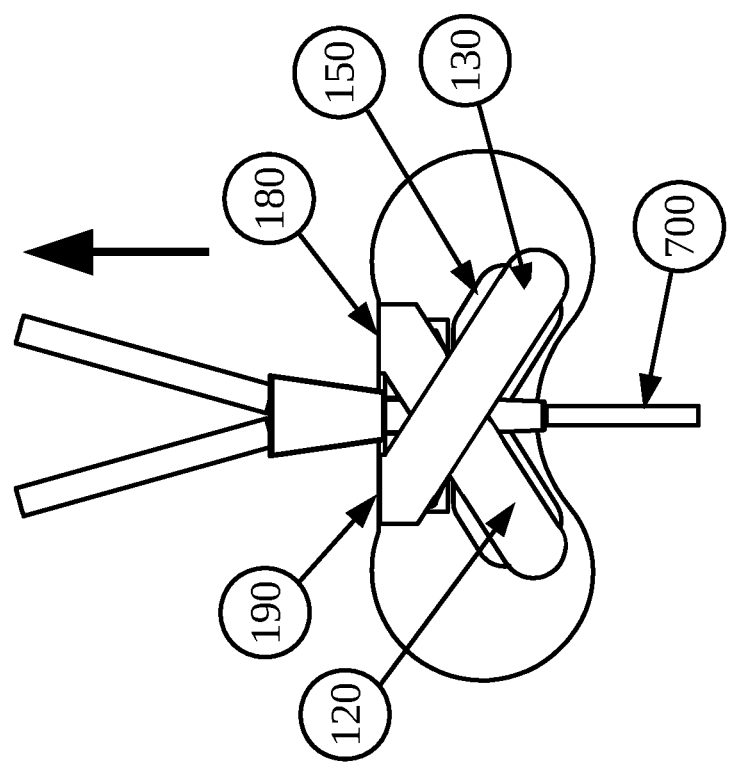
FIG. 13 is a top view of an alternative embodiment of the invention in a closed position securing a winged catheter.

Referring now to FIG. 13, the alternative embodiment of the device securing the catheter 700 in FIG. 12 is shown in the closed or chevron position. In the chevron or cross position, the strap 120 preferably crosses over the wing portion of catheter 700 and mates with the hook portion 150 of the base 100. The strap 130 crosses over the strap 120 and the wing portion of the catheter 700 and mates with the hook portion 150 of the base 100 on an opposite side of the base 100. The catheter 700 is secured between base 100, straps 120 and 130, and articulation points 180 and 190. The articulation points 180 and 190, when placed against the wing structure of catheter 700, resist dislodgment of the catheter 700 when longitudinal pull force is applied (direction of arrow in FIG. 13), while the crossover of the straps 120 and 130 and the straps 120, 130 mating to the hook portion 150 of the base 100 prevents catheter dislodgement when a lateral pull force is applied. The crossover of the straps 120 and 130 preferably produce a choke-like grip on the catheter 700 and prevent or resist catheter dislodgement.

Figure 14A:
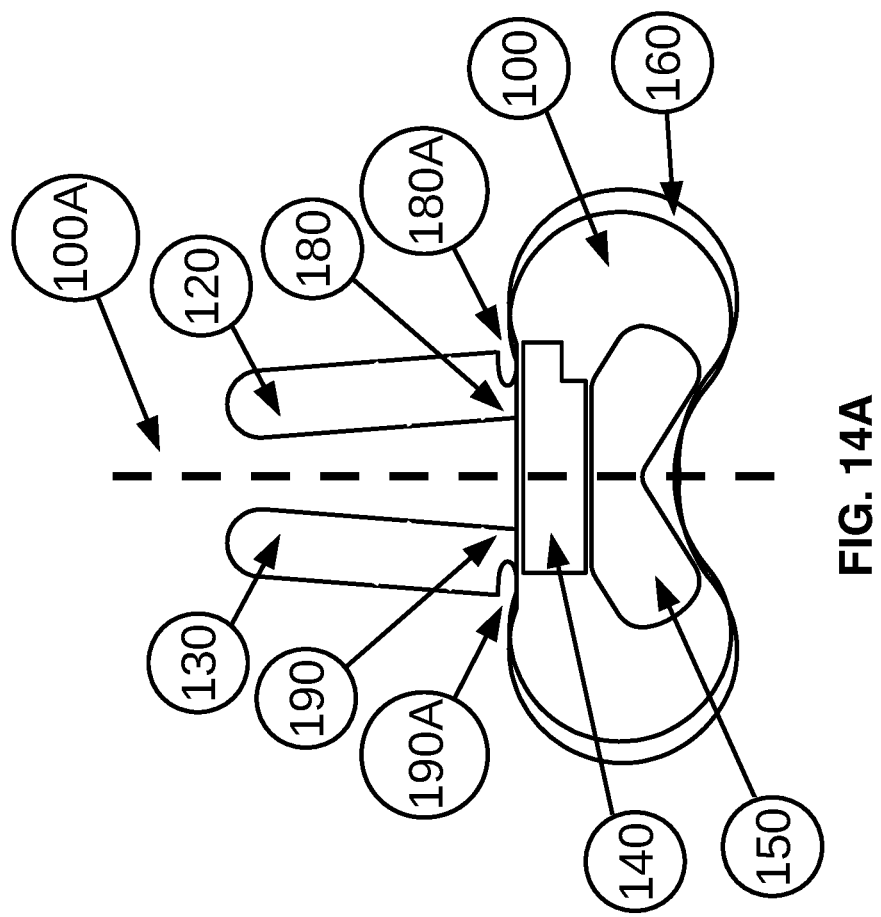
FIG. 14A is a top view of an alternative embodiment of the invention in an open position.
Figure 14B:
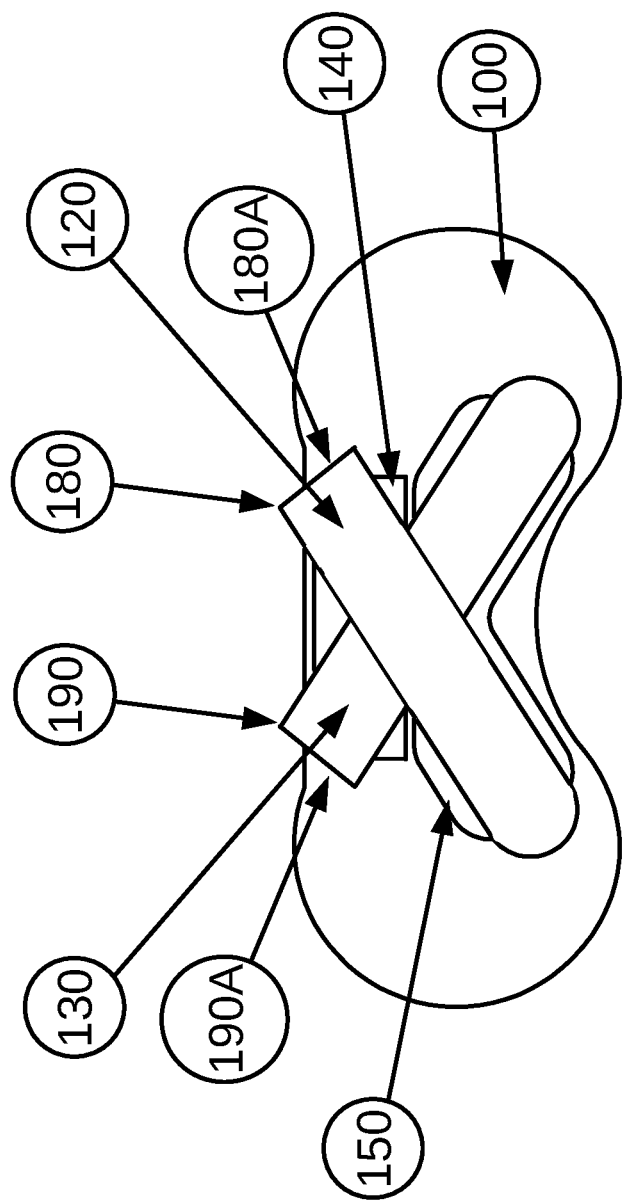
FIG. 14B is a top view of an alternative embodiment of the invention in a closed or chevron position.

Referring now FIGS. 14A and 14B, another preferred embodiment is shown. In this embodiment, straps 120 and 130 preferably do not cross center line 100A when the securement device is in an opened position. The articulation points 180 and 190 preferably have cutouts 180A and 190A. In a closed position, the cutouts 180A and 190A preferably permit articulation points 180 and 190 to obtain an angular offset in relationship to the base 100. This permits a cross over the center line 100A when being placed in the chevron position shown in FIG. 14B. This embodiment provides for a variable angle articulation point when compared to a fixed angle articulation point presented in the embodiment shown in FIG. 8A.

Figure 15B:
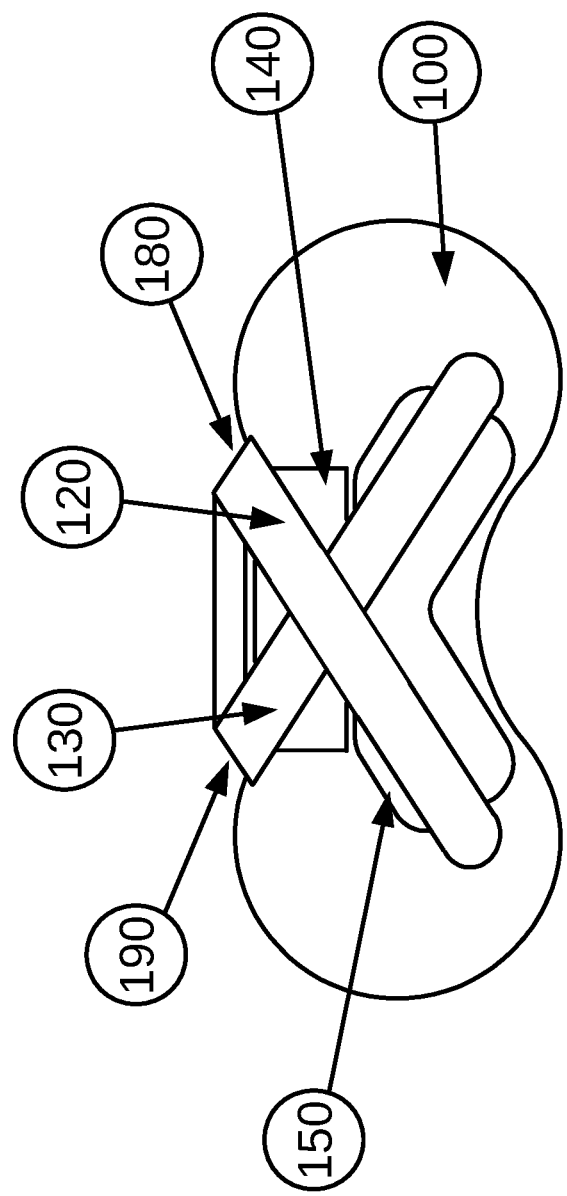
FIG. 15B is a top view of an alternative embodiment of the invention in a closed or chevron position.

Referring now to FIGS. 15A and 15B, another preferred embodiment is shown. In this embodiment, straps 120 and 130 preferably do not cross the center line 100A when the securement device is in an opened position as shown in FIG. 15A. When in a closed position, as shown in FIG. 15B, a distance between outside and inside strap edge contact point to the base creates fixed articulation angles 180A and 190A. The preferred articulation angle is 30-45 degrees. The fixed articulation angles (180A and 190A) are preferably established when straps 120 and 130 cross over the center line 100A and form a chevron position as shown in FIG. 15B.

Thus, an improved flexible universal catheter securement device is described above. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A flexible universal catheter securement device comprising:
   a base defining a center line;
   a first cross strap attached to the base at a first longitudinal articulation point; and
   a second cross strap attached to the base at a second longitudinal articulation point;
   wherein the first cross strap is movable from a first unfolded position, in which the first cross strap is flattened and extends away from the base, to a first folded position, in which the first cross strap is folded over the base,
   wherein the second cross strap is movable from a second unfolded position, in which the second cross strap is flattened and extends away from the base, to a second folded position, in which the second cross strap is folded over the base, and
   wherein, when the first cross strap is in the first unfolded position and the second cross strap is in the second unfolded position, the first cross strap converges toward but does not cross the center line as the first cross strap extends away from the base, and the second cross strap converges toward but does not cross the center line as the second cross strap extends away from the base.

2. The flexible universal catheter securement device according to claim 1, wherein:
   the first cross strap comprises a first outside edge and a first cutout at the first outside edge, and
   the second cross strap comprises a second outside edge and a second cutout at the second outside edge.

3. The flexible universal catheter securement device according to claim 2, wherein the first cutout and the second cutout permit a lateral movement of the first cross strap and the second cross strap, respectively, away from the center line.

4. The flexible universal catheter securement device according to claim 3, wherein the lateral movement permits the first cross strap and the second cross strap to cross the center line when moved to the first closed position and the second closed position, respectively.

5. The flexible universal catheter securement device according to claim 4, wherein the first cross strap and the second cross strap each cross at a variable angle in the closed position.

6. The flexible universal catheter securement device according to claim 5, wherein the variable angle is changed by changing the first cutout and the second cutout.

* * * * *